US011026585B2

(12) United States Patent
Fernald et al.

(10) Patent No.: US 11,026,585 B2
(45) Date of Patent: Jun. 8, 2021

(54) SYSTEM AND METHOD FOR INTRAOPERATIVE VIDEO PROCESSING

(71) Applicants: Bradley Allan Fernald, Toronto (CA); Gal Sela, Toronto (CA); Neil Jeffrey Witcomb, Toronto (CA)

(72) Inventors: Bradley Allan Fernald, Toronto (CA); Gal Sela, Toronto (CA); Neil Jeffrey Witcomb, Toronto (CA)

(73) Assignee: Synaptive Medical Inc., Toronto (CA)

( * ) Notice: Subject to any disclaimer, the term of this patent is extended or adjusted under 35 U.S.C. 154(b) by 47 days.

(21) Appl. No.: 16/432,404

(22) Filed: Jun. 5, 2019

(65) Prior Publication Data
US 2019/0365252 A1 Dec. 5, 2019

Related U.S. Application Data

(60) Provisional application No. 62/681,045, filed on Jun. 5, 2018, provisional application No. 62/681,052, filed on Jun. 5, 2018.

(51) Int. Cl.
G06K 9/00 (2006.01)
A61B 5/02 (2006.01)
G06T 7/00 (2017.01)
G06T 7/11 (2017.01)
G06T 7/90 (2017.01)
G06K 9/32 (2006.01)
G06K 9/62 (2006.01)
A61B 5/103 (2006.01)
(Continued)

(52) U.S. Cl.
CPC .......... A61B 5/02042 (2013.01); A61B 5/004 (2013.01); A61B 5/0077 (2013.01); A61B 5/1032 (2013.01); A61B 5/7282 (2013.01); A61B 5/7425 (2013.01); G06K 9/32 (2013.01); G06K 9/6228 (2013.01); G06T 7/0012 (2013.01); G06T 7/11 (2017.01); G06T 7/90 (2017.01); H04N 5/445 (2013.01); A61B 2505/05 (2013.01); A61B 2576/00 (2013.01); G06K 2209/05 (2013.01); G06T 2207/10016 (2013.01); G06T 2207/30008 (2013.01); G06T 2207/30096 (2013.01); G06T 2207/30101 (2013.01)

(58) Field of Classification Search
None
See application file for complete search history.

(56) References Cited

U.S. PATENT DOCUMENTS

2012/0143182 A1\* 6/2012 Ullrich ............... A61B 18/1445 606/45
2014/0093150 A1\* 4/2014 Zalev ..................... A61B 5/725 382/131

(Continued)

Primary Examiner — Hadi Akhavannik
(74) Attorney, Agent, or Firm — Ridout & Maybee LLP

(57) ABSTRACT

A monitoring method and system for providing visual enhancements during a medical procedure is described. The method includes capturing current visual information of a site during the medical procedure in real time, storing at least a portion of the captured visual information as stored visual information, identifying a feature of interest in at least one of the current visual information and the stored visual information; generating feedback data associated with the feature of interest, and displaying a virtual representation of the feedback data overlaid on the current visual information.

18 Claims, 11 Drawing Sheets

(51) Int. Cl.
*A61B 5/00* (2006.01)
*H04N 5/445* (2011.01)

(56) References Cited

U.S. PATENT DOCUMENTS

| | | | | |
|---|---|---|---|---|
| 2014/0142422 A1* | 5/2014 | Manzke | ............. | A61B 1/00149 |
| | | | | 600/424 |
| 2014/0347353 A1* | 11/2014 | Popovic | ................ | G06T 11/006 |
| | | | | 345/419 |
| 2016/0191887 A1* | 6/2016 | Casas | ................... | H04N 13/156 |
| | | | | 348/47 |
| 2017/0112577 A1* | 4/2017 | Bonutti | .................. | A61B 34/20 |
| 2020/0273548 A1* | 8/2020 | Wolf | ...................... | G16H 50/20 |

* cited by examiner

SYSTEM AND METHOD FOR INTRAOPERATIVE VIDEO PROCESSING

CROSS-REFERENCE TO RELATED APPLICATIONS

The present disclosure claims priority from U.S. provisional patent application No. 62/681,045, filed Jun. 5, 2018; and U.S. provisional patent application No. 62/681,052, filed Jun. 5, 2018, the entireties of which are hereby incorporated by reference.

FIELD

The present disclosure relates to methods and systems for providing intraoperative video processing and feedback, including providing visuospatial historical analysis and feedback, using imaging processing and visual overlay.

BACKGROUND

Surgical resection is a challenging procedure, which typically requires effective access to, and visualization of, a surgical site. This activity is frequently complicated by insufficient illumination or artefacts which obscure the resection site. This is particularly true as surgical approaches have moved from traditional "open" procedures to newer and more demanding "minimally invasive" procedures utilizing small openings. In an example neurosurgical procedure, a surgeon or a robotic surgical system may perform a port-based minimally-invasive procedure involving tumor resection in the brain.

In conventional procedures, the surgeon is typically provided with a view of the site of interest via a camera or eyepiece of a microscope, endoscope or exoscope. This naturally provides only a real-life, current view of the actual site, without any additional visuospatial information that might help the surgeon. Instead, the surgeon is required to turn to other screens or monitors for additional information, or rely on their own trained visuospatial abilities. This can be taxing to the surgeon and may lead to longer procedures and greater risk of accidental trauma to healthy tissue.

In addition, surgeons are required to exert significant focus and physical control to achieve highly precise interventions on their patients. This may result in "focus bias", where the surgeon is unable to notice signals which may indicate emerging issues outside of the immediate surgical focus.

SUMMARY

In some examples, the present disclosure provides a monitoring system for providing visual enhancements during a medical procedure, the system comprising: a sensor for capturing current visual information of a site during the medical procedure in real time; a memory for storing at least a portion of the visual information as stored visual information; a display for displaying the current visual information; and a processor coupled to receive the current and stored visual information from the sensor and the memory, and coupled to transmit output data for display on the display, the processor being configured to: identify a feature of interest in at least one of the current visual information and the stored visual information; generate feedback data associated with the feature of interest, using the current visual information and the stored visual information; and cause the display to display a virtual representation of the feedback data overlaid on the current visual information.

In some examples, the present disclosure provides a system for reacting to an event during a medical procedure, the system comprising: an implementation system configured to perform the medical procedure and to perform predetermined steps in response to the event; and the monitoring system described above coupled to the implementation system, wherein the feedback data includes indication that the event has occurred; and the monitoring system configured to: analyze the current visual information to detect occurrence of the event; signal the implementation system to pause the medical procedure and initiate the predetermined steps in response to the event; and when the event is no longer detected, signal the implementation system to resume the medical procedure.

In some examples, the present disclosure provides a monitoring method for use during a medical procedure, the method comprising: capturing current visual information of a site during the medical procedure in real-time; storing at least a portion of the captured visual information as stored visual information; identifying a feature of interest in at least one of the current visual information and the stored visual information; generating feedback data associated with the feature of interest, using the current visual information and the stored visual information; and displaying a virtual representation of the feedback data overlaid on the current visual information.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
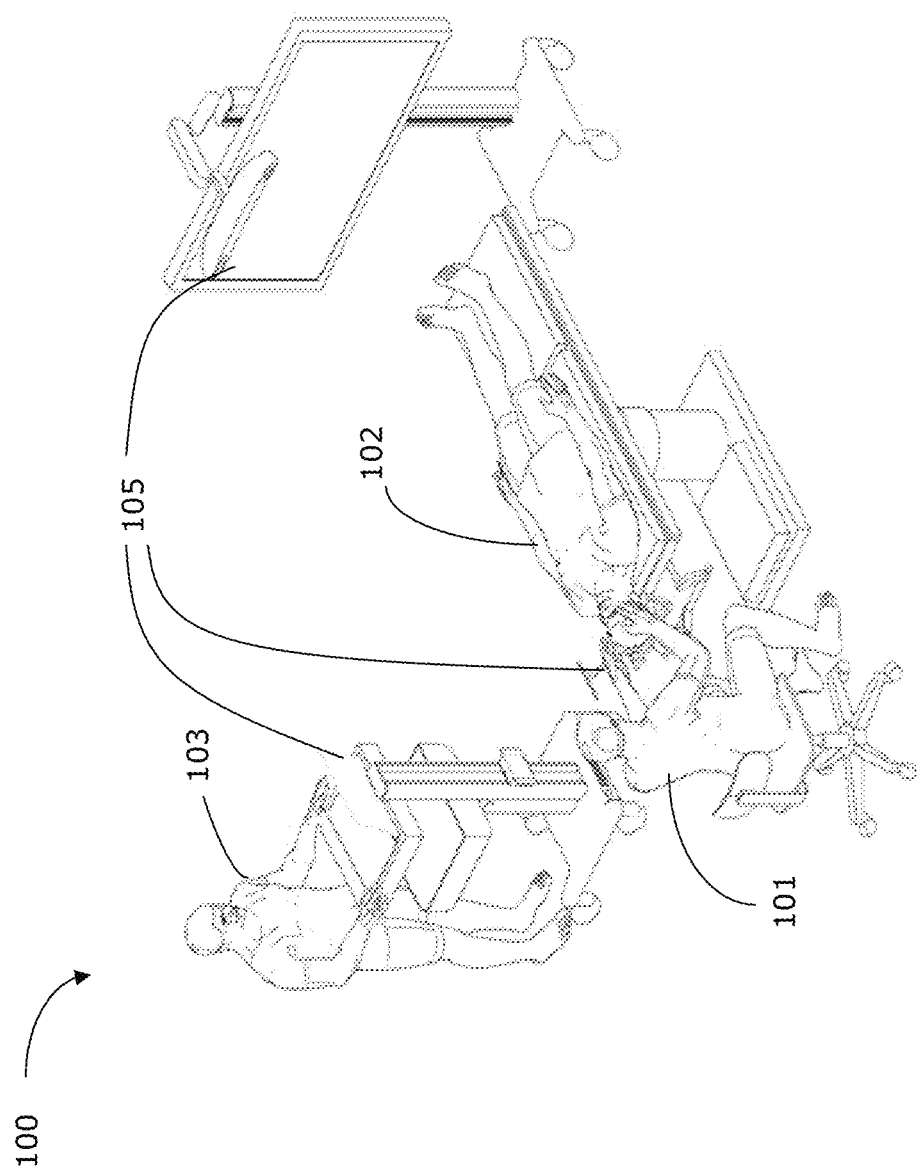
FIG. 1 shows an example operating system to support image guided surgery.

The present disclosure describes a system and method which provide visualization and which uses a digital capture system to, among other things, intraoperatively identify specific areas or features of interest and then enhances them, or selectively identifies and de-emphasize artefacts. These could also be shared with connected systems for additional processing/behavior such as a Navigation System (an example of a navigation system is described in U.S. patent application Ser. No. 15/650,253, the entirety of which is hereby incorporated by reference). Further, the present subject matter may be used in combination with certain intra-op modalities, including Doppler ultrasound, digital subtraction angiography (DSA), electrocardiography (ECG), etc. The processing can be performed by the imaging system itself, or the video stream can be fed to another system (such as a surgical navigation system) which can provide further processing in combination with data available within that other system (e.g. registered preoperative magnetic resonance imaging (MRI)/computed tomography (CT) data). Additionally with further processing, the system can quantify certain characteristics of the area of interest.

This system may be used in conjunction with medical procedures involving access ports, catheters, deep brain stimulation (DBS) needles, a biopsy procedure, and also to biopsies and/or catheters in other medical procedures performed on other parts of the body, as well as to medical procedures that do not use an access port, including non-neural medical procedures, such as spinal procedures.

The systems and methods described herein may be useful in medical procedures, including surgical procedures. The present disclosure provides examples in the field of neurosurgery, such as for oncological care, treatment of neurodegenerative disease, stroke, and brain trauma. Persons of skill will appreciate the ability to extend these concepts to other conditions or fields of medicine. For example, the present disclosure may also be applicable to the field of spinal surgery or orthopedic surgery, among others. It should be noted that while the present disclosure describes examples in the context of neurosurgery, the present disclosure may be applicable to other procedures that may benefit from intraoperative video analysis and providing virtual visual information during the medical procedure.

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not an embodiment of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein the phrase "preoperative" refers to an action, process, method, event or step that occurs prior to the start of a medical procedure. Preoperative, as defined herein, is not limited to surgical procedures, and may refer to other types of medical procedures, such as diagnostic and therapeutic procedures. Planning a medical procedure may be considered to be preoperative.

Some embodiments of the present disclosure include imaging devices that are insertable into a subject or patient for imaging internal tissues, and methods of use thereof. Some embodiments of the present disclosure relate to minimally invasive medical procedures that are performed via an access port or retractor tube, whereby surgery, diagnostic imaging, therapy, or other medical procedures (e.g., minimally invasive medical procedures) are performed based on access to internal tissue through the access port or retractor tube.

System

In FIG. 1, an exemplary operating system 100 environment is shown, which may be used to support image-guided surgery. As shown in FIG. 1, a surgeon 101 conducts a surgery on a patient 102 in an operating room (OR) environment. A medical monitoring system 105 for providing visual enhancements during a medical procedure may include an equipment tower, a sensor, and displays to assist the surgeon 101 during the procedure. An operator 103 may also be present to operate, control and provide assistance for the medical monitoring system 105.

Figure 2:
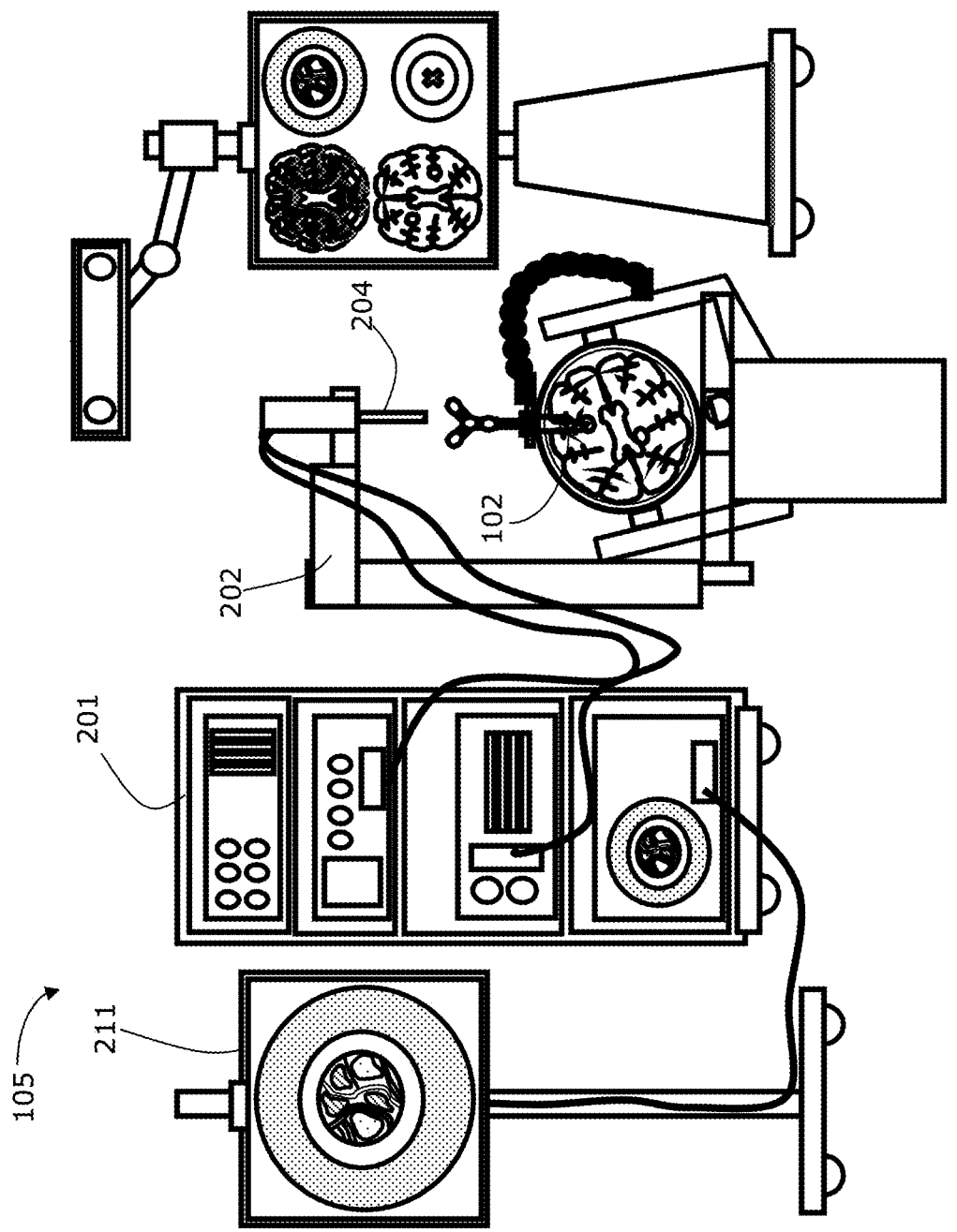
FIG. 2 is a diagram illustrating system components of an example monitoring system.

FIG. 2 shows a diagram illustrating components of the example medical monitoring system 105. The disclosed methods and systems for providing visuospatial information may be implemented in the context of the medical monitoring system 105. The medical monitoring system 105 may include a positioning system 202 (e.g. a mechanical arm), which may support a sensor for capturing current visual information of a site during the medical procedure in real time. In the depicted embedment, the sensor is an optical scope (which may also be referred to as an external scope or camera 204). The camera 204 is configured to capture a video with current and past frames of a field-of-view (FOV) of the site during the medical procedure. Preferably, the camera 204 captures a high-resolution, high-frame-rate video of the surgical site and may include a stereoscopic configuration. Illumination and video capture may utilize sources and filters which enable capture outside of the normal human range (e.g. Hyper-spectral, fluorescence, etc.)

The camera 204 may be attached to the positioning system 202, and may be used to view down an access port 102, for example, at a sufficient magnification to allow for enhanced visibility down the access port 102. The output of the camera 204 may be received by one or more computers or controllers, such as those part of the equipment tower discussed below, to generate a view that may be depicted on a visual display (e.g., one or more displays 211).

The one or more displays 211 are for displaying the current visual information and/or the stored visual information, including still and/or video images (e.g., a live video image of the surgical field and/or 2D or 3D images obtained preoperatively). The one or more of the displays 211 may include a touch-sensitive display for receiving touch input.

The display 211 may also provide output of the computed data of the monitoring system 105. In some examples, the output provided by the display 211 may include axial, sagittal and coronal views of patient anatomy as part of a multi-view output. In some examples, the one or more displays 211 may include an output device, such as a wearable display device, to provide an augmented reality (AR) display of the site of interest.

The monitoring system 105 further includes an equipment tower 201. The equipment tower 201 may be mounted on a frame (e.g., a rack or cart) and may contain a power supply and a computer or controller that may execute planning software, monitoring software and/or other software to manage the camera 204. In some examples, the equipment tower 201 may be a single tower configuration operating with multiple displays 211, however other configurations may also exist (e.g., multiple towers, single display, etc.). Furthermore, the equipment tower 201 may also be configured with a universal power supply (UPS) to provide for emergency power, in addition to a regular AC adapter power supply.

Figure 3:
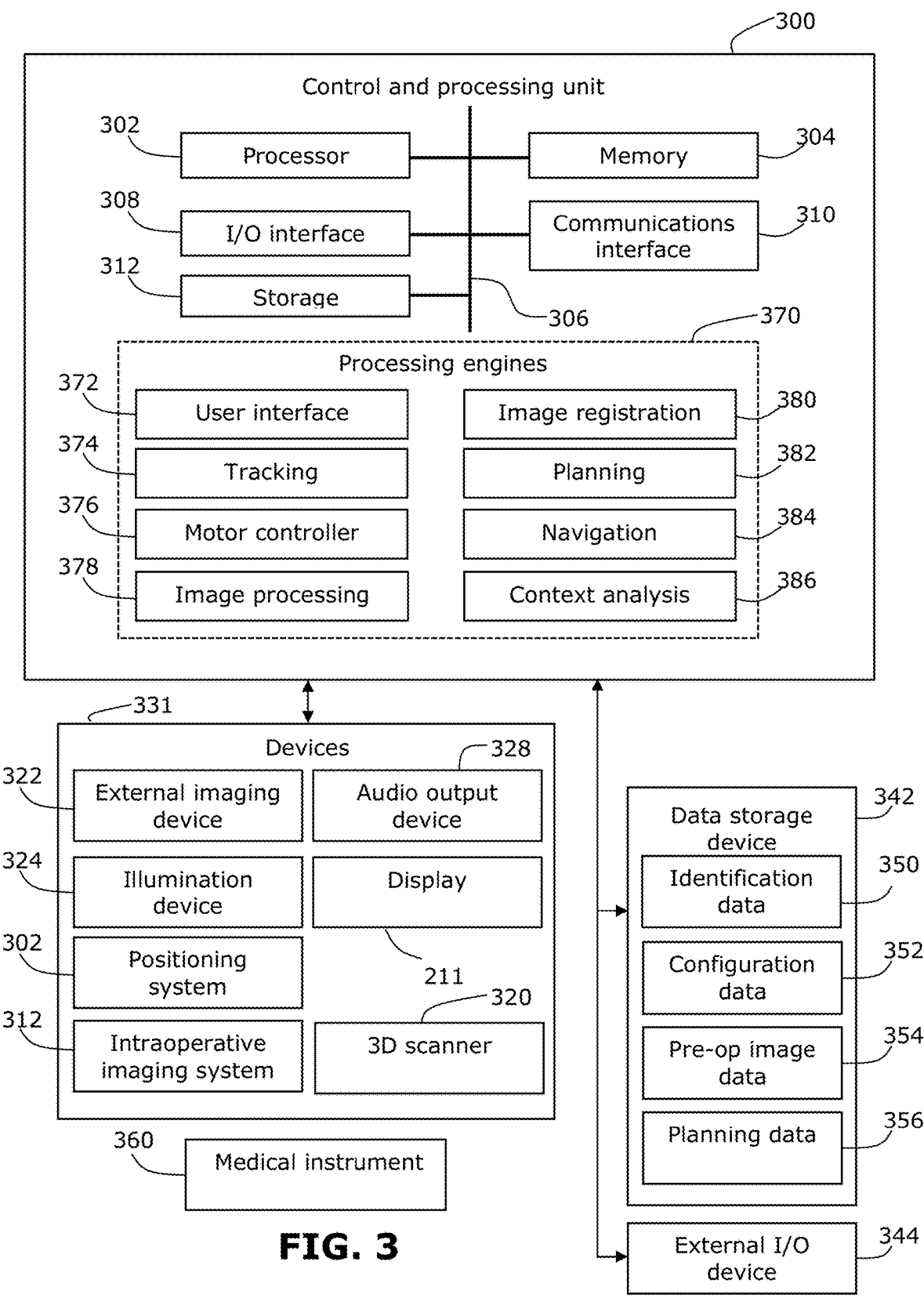
FIG. 3 is a block diagram illustrating an example control and processing system that may be used in the monitoring system of FIG. 2.

In FIG. 3, a block diagram is shown illustrating a control and processing system 300 that may be used in the medical monitoring system 105 shown in FIG. 2 (e.g., as part of the equipment tower). As shown in FIG. 3, in an example, the control and processing system 300 may include one or more processors 302, a memory 304, a system bus 306, one or more input/output interfaces 308, a communications interface 310, and a storage device 312. The control and processing system 300 may provide other functions in addition to medical monitoring. For example, the control and processing system 300 may provide navigation functions, tracking functions, planning functions, etc.

The control and processing system 300 may be interfaced with other external devices, such as data storage 342, and external user input and output devices 344, which may include, for example, one or more of a display, keyboard, mouse, sensors attached to medical equipment, foot pedal, and microphone and speaker. The data storage 342 may be any suitable data storage device, such as a local or remote computing device (e.g. a computer, hard drive, digital media device, or server) having a database stored thereon. In the example shown in FIG. 3, the data storage device 342 includes identification data 350 for identifying one or more medical instruments (e.g., a tracked tool, such as a pointing tool) and configuration data 352 that associates customized configuration parameters with one or more of the medical instrument(s) 360. The data storage device 342 may also include preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The control and processing unit 300 may also interface with a number of configurable devices, and may intraoperatively reconfigure one or more of such devices based on configuration parameters obtained from the configuration data 352. Examples of devices 331, as shown in FIG. 3, include one or more external imaging devices 322, one or more illumination devices 324, a positioning system 202 (e.g., a robotic arm), an imaging device 312, one or more audio output devices 328, one or more displays 211, and a scanner 320, which in an example may be a 3D scanner.

Exemplary aspects of the disclosure can be implemented via the processor(s) 302 and memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some examples the processing modules 370 may be stored in the memory 304 and the processing modules 370 may be collectively referred to as processing modules 370. In some examples, two or more modules 370 may be used together to perform a function. Although depicted as separate modules 370, the modules 370 may be embodied as a unified set of computer-readable instructions (e.g., stored in the memory 304) rather than distinct sets of instructions.

Turning now to the processor 302 and memory 304, memory 304 in the present embodiment is configured to store at least a segment of the visual information captured by the camera 204 as stored visual information. The processor 302, in turn, may be coupled to receive the current and stored visual information from the camera 204 and memory 304, and coupled to transmit output data for display on the one or more displays 211.

The processor 302 is configured, among other things, to identify a feature of interest in at least one of the current visual information and the stored visual information. In an exemplary embodiment, the processor is configured to analyze the video according to at least one of colour, texture, physical shape, and location within the FOV. Such analysis may be performed in real-time or semi-real-time.

The processor 302 may be further configured to segment an area in the at least one of the current and past frames according to the video analysis, and identify the segmented area as indicative of the feature of interest. For example, the processor 302 may use any suitable machine vision algorithm to perform image segmentation and object recognition. Machine vision may involve standard algorithmic approaches, including applying shape operators on the image, rule-based or quantification algorithms, or machine learning algorithms.

The segmented object or feature of interest may be detected automatically by the monitoring system 105, or may be identified manually through direct user input. When monitoring system 105 involves automatic detection using machine vision, for example, blood vessels could be identified algorithmically. The blood vessels could be identified through shape operators on the image, such as through looking for areas that match shape, colour, and other geometric constraints previously defined as being indicative of vessels.

When the feature of interest is a pool of blood, for example, the processor may be configured to analyze the video to detect a colour, such as a dark red colour, covering more than a threshold portion of the current frame, which the processor would identify as indicating a pool of blood in the current frame/visual information.

The processor 302 is further configured to use the current visual information with the stored visual information to generate feedback data (e.g., feedback associated with the pool of blood). The output data may be generated using any suitable machine vision approach, such as rule-based or quantification algorithms or machine-learning algorithms taught through extensive training sets, such as through an artificial intelligence component. In the case where a pool of blood has been detected, the processor 302 may review stored frames for an originating point for the pool of blood. For example, the processor 302 may compare frames to locate a stored frame showing the initial presence of an area of blood, and then calculate a bleed point (from which the pool of blood originated) as being the center of the initial area of blood, or by reverse projecting the spread of the pool of blood over time back to a point or region of origin. The feedback data may then be data indicating the location of the bleed point.

The processor 302 then causes the display 211 to display a virtual representation of the feedback data overlaid on the current frame/visual information. In the case of feedback indicating a bleed point, the overlay may be a virtual representation of the bleed point overlaid on the current frame/visual information so the surgeon can see the bleed point in spite of the visual obstruction caused by the pool of blood.

As noted above, the control and processing unit 300 may interface with a number of configurable devices, such as audio output device 328, to provide various types of feedback. For example, when the feature of interest is identified, the processor 302 may be further configured to cause an audio notification and/or a tactile notification to be provided.

It is to be understood that the system is not intended to be limited to the components shown in FIG. 3. One or more components of the control and processing system 300 may be provided as an external component or device. In one example, the navigation module 384 may be provided as an external navigation system that is used in cooperation with the control and processing system 300.

Some embodiments may be implemented using the processor 302 without additional instructions stored in memory 304. Some embodiments may be implemented using the instructions stored in memory 304 for execution by one or more general purpose microprocessors. Some embodiments may be implemented using instructions stored remotely, for example in a cloud storage. Thus, the disclosure is not limited to a specific configuration of hardware and/or software.

In some examples, the monitoring system 105, which may include the control and processing unit 300, may provide tools to the surgeon that may help to improve the performance of the medical procedure and/or post-operative outcomes. In addition to removal of brain tumours and intracranial hemorrhages (ICH), the monitoring system 105 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, examples of the present disclosure may be performed with any suitable medical procedure.

It should be noted that a guided robotic system may be used as a proxy for human interaction. Guidance to the robotic system may be provided by any combination of input sources such as image analysis, tracking of objects in the operating room using markers placed on various objects of interest, or any other suitable robotic system guidance techniques.

The above described system may be useful when the feature of interest may be within the FOV, but not within the surgeon's current area of interest (e.g., the feature of interest may be outside of the surgeon's current focus-bias and thus not receiving attention).

In some embodiments, the monitoring system 105 may be used to provide visual augmentation in surgical sites where the feature of interest may be challenging for a human to determine purely through visualization (e.g., requiring unreasonable amounts of attention to achieve), or where the feature of interest may be impossible for a human to determine purely through visualization (e.g., requiring unreasonable visual acuity or ability to discern subtle differences in colour or texture over time, or being outside the range of normal human vision).

In such cases, after current visual information is captured and stored, the processor 302 may be configured to analyze the video to detect a predetermined physical shape or dimension within the current and/or stored frames. The detection of the predetermined physical shape may segmented and identified (e.g., using any suitable machine vision algorithm) as indicative of the feature of interest, such as an anatomical structure. The anatomical structure may be one of a blood vessel, a nerve, a ligament, a bone structure and a tumour.

The feature of interest may also, or instead, involve a non-anatomical structure. An example of a non-anatomical feature of interest includes the tip of a suction device. Detecting the presence of the tip of a suction device may allow the user to change its settings on a robotic control system, or its detection may be used for tracking purposes.

The processor 302 may also be configured to cause the display 211 to display a virtual representation of the segmented anatomical structure.

The monitoring system 105 may be suitable for use during numerous types of medical procedures, including one or more of: brain biopsy, functional/deep-brain stimulation, catheter/shunt placement (in the brain or elsewhere), open craniotomies, and/or endonasal/skull-based/ear-nose-throat (ENT) procedures, as well as procedures other than neurosurgical procedures. The same monitoring system 105 may be used for carrying out any or all of these procedures, with or without modification as appropriate.

For example, the monitoring system 105 may be used during a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures may be conducted with or without a stereotactic frame. Both types of procedures may be performed using image-guidance. Frameless biopsies, in particular, may be conducted using the monitoring system 105. In a surgical operating room (or theatre), setup of an operating system may be relatively complicated; there may be many pieces of equipment associated with the medical procedure, as well as elements of the monitoring system 105. Further, setup time typically increases as more equipment is added. The surgeon 101 may be required to process many sets of information from different equipment during the medical procedure. Information may be primarily of a visual nature, and the surgeon 101 may easily be overwhelmed by the amount of information to be processed.

To assist in addressing this, the monitoring system 105 may form a part of the larger operating system 100 for detecting and reacting to an event during the medical procedure. Such a system may aid the surgeon 101 and the surgical staff by reducing the cognitive load, and may allow for faster responses, and provide focus points for study post-surgery.

The operating system 100 includes an implementation system configured to perform the medical procedure and to perform predetermined steps in response to the event, for example, a bleed. The implementation system may overlap with the monitoring system 105. For example, the implementation system may include the positioning system 202 (which may support one or more surgical instruments in addition to the camera 204), the camera 204 and/or the processor 302. The feedback data may include an indication that the event (such as a bleed) has occurred, and may trigger a response in the implementation system.

For example, when the bleed point is detected, the monitoring system 105 signals the implementation system to pause the medical procedure and initiate the predetermined steps when the event has occurred, such as a bleed. For example, the implementation system, in response to a signal that a bleed has occurred, use feedback data (e.g., indicating location of a bleed point) to change positioning and focus of the camera 204 to focus on the bleed point. When the bleed point is no longer detected, the monitoring system may signal the implementation system to resume the medical procedure. For example, the implementation system may return to the previous camera position and focus. The skilled person would understand that the event may be any medical event, including tissue becoming hypoxic, for example.

Figure 4:
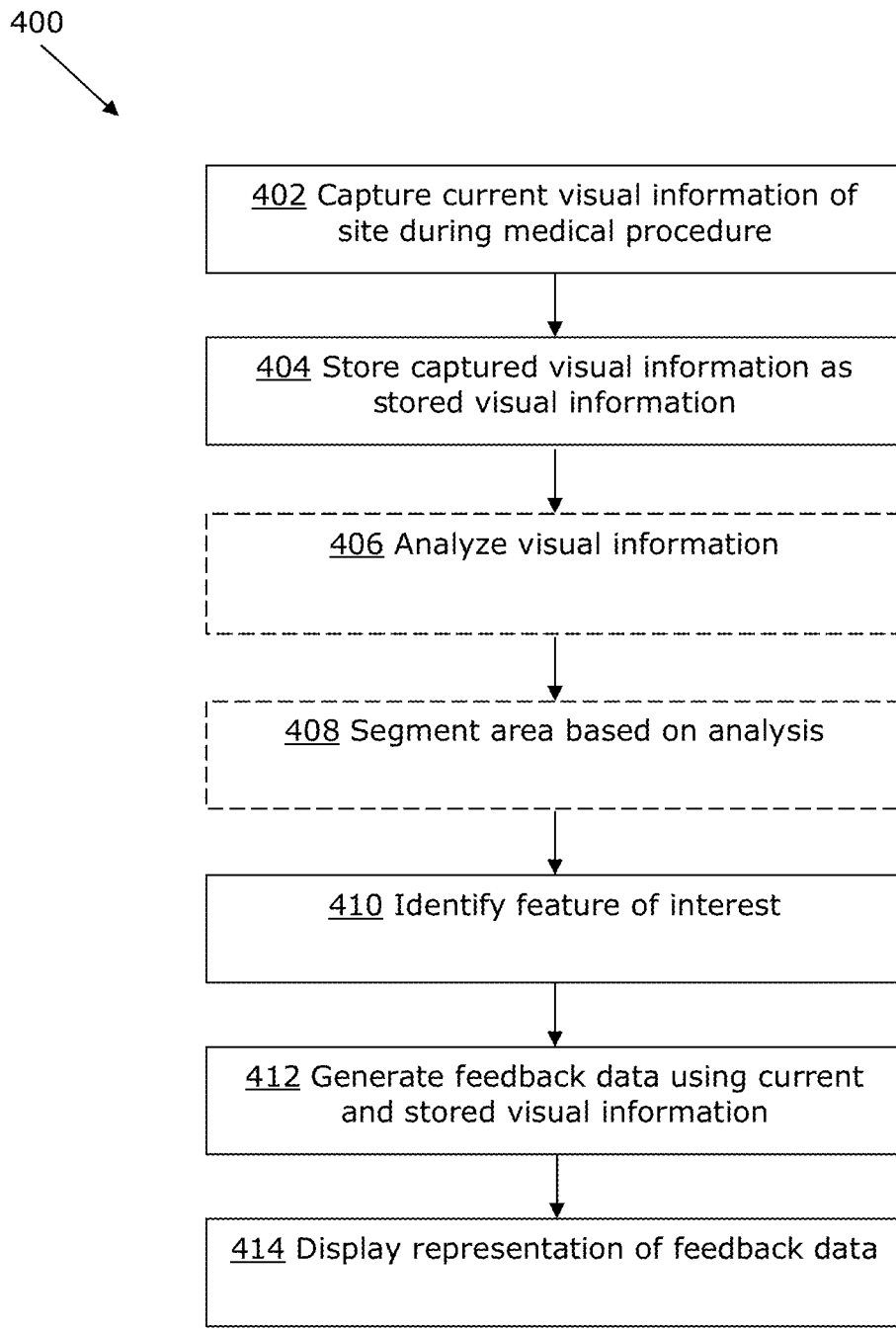
FIG. 4 is a flowchart illustrating an example method for providing intraoperative visuospatial feedback information.

FIG. 4 is a flowchart illustrating an example monitoring method 400 for providing feedback during a medical procedure, for example using the monitoring system 105 described above. The following discussion of method 400 may lead to further understanding of monitoring system 105. However, it is to be understood that monitoring system 105, and method 400 can be varied, and need not work exactly as discussed herein in conjunction with each other, and that such variations are within scope of the appended claims.

Figure 6:
FIG. 6 shows an example of a current captured image/frame of a video taken during a medical procedure without any virtual representation.

The example method 400 may be implemented intraoperatively, for example during a minimally invasive procedure FIG. 6 shows an example of a minimally invasive cranial procedure. Such procedures may be performed to address a skull base tumor or vascular malformation (such as an aneurism.

An example implementation of the method 400 will be described below with reference to FIG. 6. Other example implementations will also be provided further below.

The method 400 may take place in the context of an image-guided medical procedure.

At 402, camera 204 captures current visual information of the surgical site during the medical procedure in real-time. At 404, at least a portion of the captured visual information is stored in memory 304 as stored visual information.

For example, the capturing may comprise filming a video of a field-of-view (FOV) of the site during the medical procedure. In this regard, the current visual information captured is the current frame and the stored visual information in memory 304 are one or more past frames. FIG. 6 is an example of a current frame taken during the procedure that is eventually stored in memory 304 as one of the stored frames.

At 406, the method 400 may include analyzing the video according to a visual characteristic, including at least one of colour, texture, physical shape, and location within the FOV.

For example, the system may analyse visible characteristics of the object of interest such as: apparent colour (including wavelengths outside of normal visual range), differential colour, texture, differential texture, physical dimensions, shape and morphology (morphometry), changes (possibly cyclical) in morphology including those deliberately introduced (for example moving bony anatomy to record changes to tendons and ligaments) and structural organization (for example as measured using Optical Coherence Tomography (OCT)).

The analysis may also involve detecting biomarkers of the feature of interest, including using contrast agents or other bio-markers, such as fluorescence due to markers such as ICG, 5-ala and others, and spectrographic signal (requiring excitation by a laser delivered through the system such as Raman Spectroscopy).

At 408, following the analyzing, the method may further include segmenting an area in at least one of the current and past frames according to the video analysis. The segmented area may indicate a feature of interest that is identified at 410. The segmented object or feature of interest may be detected automatically by the monitoring system 105 (e.g., using machine vision), and/or may involve user input (e.g., selection of an area or image segment of interest via user interaction with a touch-sensitive display or other user interface).

Following the bleed example introduced above, the feature of interest to be identified may be a pool of blood 600 in the current visual information/video frame. In such a case, the analyzing 406 may include detecting a dark red colour which covers more than a threshold portion of the current frame and/or of one of the stored frames or is detected to be increasing in area over two or more consecutive frames. This threshold qualification may be set to distinguish a growing pool of blood that requires attention from other more innocuous, static patches of blood that may be present in the surgical site.

At 408, therefore, the threshold portion of the current and/or stored frame that is dark red in colour may be determined and segmented. This segmented area of a dark red colour is indicative of, or represents, a pool of blood, and is thus identified as the feature of interest in 410.

While analyzing and segmenting of the video may be used to help identify the feature of interest (or pool of blood), the analyzing and segmenting by a processor are optional. For example, the pool of blood may instead be visually identified by the operator 103 on the display 211. The presence of the pool of blood 600 may then be inputted into the monitoring system 105 via any input devices, including the touch-sensitive display for receiving touch input on the display 211.

Once the feature of interest is identified, feedback data associated with the feature of interest is generated at 412, using the current and stored visual information. The feedback data may be generated using quantification algorithms or machine-learning algorithms taught through extensive training sets. In some examples, a comparison of video frames may be performed.

Figure 7:
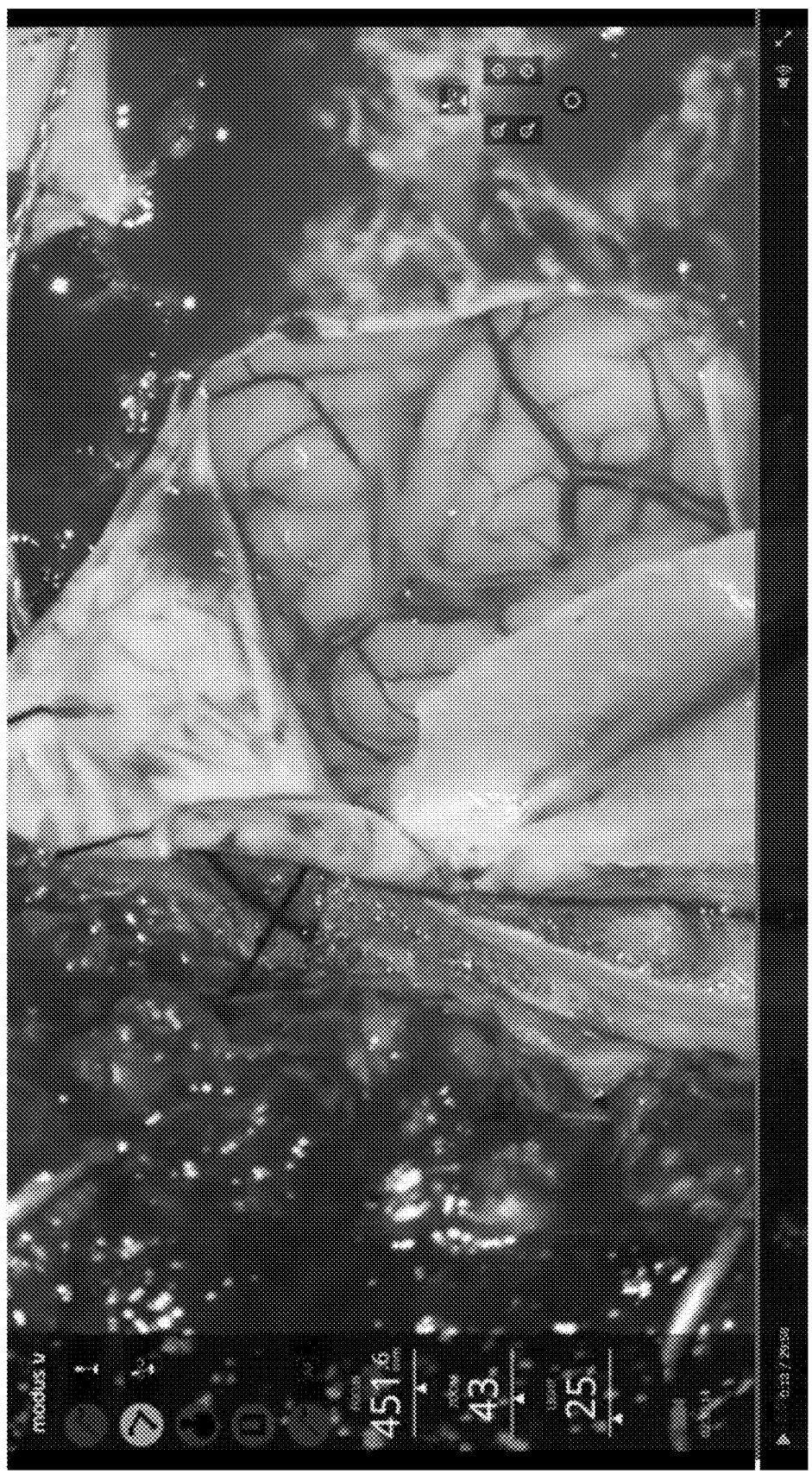
FIG. 7 shows an example of a stored image/frame taken prior to FIG. 6.
Figure 8:
FIG. 8 shows an example of another stored image/frame taken prior to FIG. 6.

Returning to the bleed scenario, an example of the feedback data generated is an indication of a location of a bleed point. When the pool of blood 600 is identified, the current frame (FIG. 6 for example) may be reviewed and compared with one or more stored frames (FIGS. 7 and 8 for example) that were taken prior to the current frame. Based on a review of the stored frames and the smaller area the pool of blood covered in FIGS. 7 and 8, the location of the bleed point or bleed source may be located.

Figure 9:
FIG. 9 shows the current image/frame of FIG. 6 with a virtual representation overlaid thereon.

Once the feedback data is generated, a virtual representation of the feedback data may be overlaid on the current visual information and displayed on display 211, at 414. For example, as shown in FIG. 9, FIG. 9 shows the same current frame as FIG. 6, however, FIG. 9 includes a virtual representation of the bleed point in the form of an arrow overlaid on the current frame. In this manner, the surgeon 101 can see the location of the bleed point in spite of the visual obstruction caused by the pool of blood in the current frame.

The monitoring method 400 may further include other types of feedback, such as providing an audio or tactile notification to the surgeon 101 when the pool of blood and/or the bleed point is identified by the monitoring method 400. Such other types of feedback may be helpful if, for example, the surgeon is focused on a particular site, and the bleed occurs in a site that is out of visual range. For example, the operating system may further include an additional camera with a wider or different field of view to capture additional visual information. In some examples, the operating system could also extrapolate a bleed point that is outside of the primary video frame/current visual information, for example based on the detected motion and/or expansion of the pool of blood that is visible in the primary frame.

In some examples, the monitoring method 400 may be used to provide visual augmentation in surgical sites where the feature of interest may be challenging for a human to determine purely through visualization (e.g., requiring unreasonable amounts of attention to achieve), or where the feature of interest may be impossible for a human to determine purely through visualization (e.g., requiring unreasonable visual acuity or ability to discern subtle differences in colour or texture over time, or outside the range of human vision).

In such cases, after current visual information is captured at 402 and stored at 404, the analyzing at 406 may comprise detecting a predetermined physical shape, or dimension within the current and/or stored frames using any of the analysis techniques described above. The presence of a detected predetermined physical shape within the frame may be indicative of, or represent, an anatomical structure. The detection of the predetermined physical shape may thus be identified as the feature of interest in 410. The anatomical structure may be one of a blood vessel, a nerve, a ligament, a bone structure and a tumour.

Figure 10:
FIG. 10 shows another example of a current captured image/frame of a video taken during another medical procedure without any virtual representation.
Figure 11:
FIG. 11 shows the current captured image/frame of FIG. 10 with a feature of interest highlighted.

At 412, the feedback data may be generated using the current frame and stored frames. For example, a review of stored frames may be performed to confirm that the identified physical shape is indeed an existing anatomical structure, and not an artefact for example. The display may then be a display of a virtual representation of the anatomical structure itself at 414. For example, FIG. 10 shows a current frame without any feedback data. It is difficult to discern a structure of interest, either anatomical or non-anatomical, in this frame. Using the method described above, a non-anatomical structure of interest (such as a medical instrument) may be identified, segmented and shown as a virtual representation (e.g., a highlighted area) as illustrated by FIG. 11.

Further to the visual feedback described above, the present method may also provide other types of feedback (e.g., in an audio or tactile manner), for example warning when a tracked surgical tool is going too close to an identified blood vessel.

Figure 5:
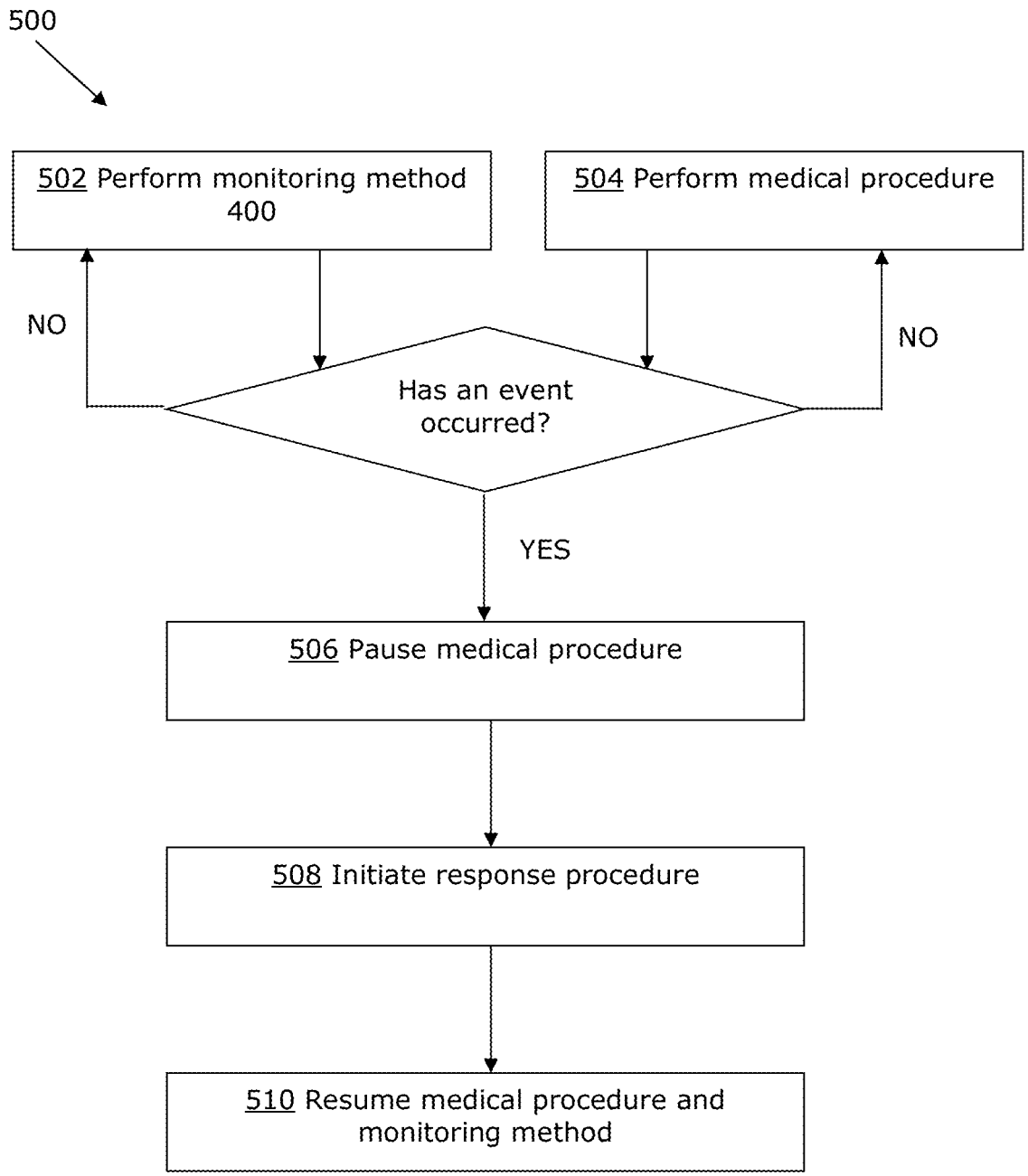
FIG. 5 is a flowchart illustrating an example method for reacting to the intraoperative visuospatial feedback information.

FIG. 5 is a flowchart illustrating an example method 500 for reacting to an event during a medical procedure, and of how the monitoring method 400 may be performed in conjunction with the performance of the medical procedure. The monitoring method 400 is typically performed at 502 at the same time as the performance of the medical procedure at 504. Here, the feedback data generated in the monitoring method 400 may include an indication that the event, such as a bleed, has occurred.

In the bleed scenario, after occurrence of a bleed has been identified in the monitoring method 400, the medical procedure is paused at 506 and a response procedure, such as a bleed response procedure, is initiated at 508. The bleed response procedure may include, for example, the implementation system changing the FOV and/or magnification of the camera to focus on the bleed point during the bleed response procedure. If specific settings on surgical equipment are required to handle the bleed, such as a specific bipolar setting, the implementation system may automatically change the setting of the surgical equipment to help reduce the burden on the staff and allow the surgeon to enact a faster response.

Once the bleed has been addressed, or the event is otherwise no longer detected, the implementation system may resume the medical procedure (e.g., by returning to the settings prior to detection of the event) and the monitoring method 400 is resumed at 510.

Further embodiments, examples and variations to the above described systems and methods are possible and described below.

Analysis and Segmentation Techniques

Other techniques for characteristic detection (for example, anticipated diameter, pulsation, multi-spectral signature, etc.) may also be used to analyze, detect and segment anatomical structures which may be directly visible to the camera 204. Additionally, machine-learning algorithms can be taught to processor 302 to recognize characteristic parameters of blood vessels through extensive training sets. More sophisticated multi-parametric analysis may also be used. For example the system may highlight areas of a certain colour and a certain pulsation as blood vessels.

It is also possible to use tracking data and pre-segmented (or auto segmented) structures that exist in existing navigation data (such in MRI or CT imaging) or that can be processed from such navigation data (e.g. perfusion information from MRI contrast data) in order to infer what may be visible in the video and to assist the video-based auto-segmentation.

When identifying sub-surface vessels, the position and orientation of sub-surface vessels may be inferred by analyzing the video of the site. Amplitude and frequency of tissue deformation in the video may be correlated with certain sizes and types of blood vessel. These locations may be marked as possible locations of vessels. This information may help the surgeon 101 to be more cautious with resection devices, such as mechanical or energy devices, that may damage tissues beyond what is currently visible.

Regarding nerves, nervous tissue is highly vulnerable during resection and can be quite difficult to identify from direct visualization. Surgeons frequently must resort to electrical stimulation in order to deduce how close they are to anticipated structures. Advanced imaging platforms (such as Polarized OCT) may be used to recognize and identify these structures so that their location can be overlaid over traditional white-light video feed.

Regarding ligaments, ligaments and tendons are soft tissue structures surrounding and connecting to bony anatomy and are responsible for maintaining structural integrity and dynamic integrity of the bony anatomy. The location of the ligaments and tendons, and the alignment and integrity of the fibrous structure composing the ligaments and tendons may be better understood by using white light or a combination of white light and structural scanning (i.e. OCT), and by tracking the dynamic changes of these, including the path, through motion. This may help the surgeon 101 understand how surgical decisions are impacting dynamic control for the patient following surgery. This could be combined with a targeted preoperative plan to optimize ligament balancing or assess tendon repair.

To identify bony landmarks, structural characteristics may be detected, including colour or multi-spectral signatures. In this manner, it may be possible to identify bony structures and landmarks such as bone, cartilage and specific objects, such as vertebral bodies and their substructures (spinus process, etc.)

Image-based analysis may be used to identify specific bony features and provide further information to the surgeon. For example, the individual vertebrae in the spine could be identified, numbered and displayed as the virtual representation on the display 211, providing global orienting information to the surgeon 101 focusing on a highly magnified image showing a limited field-of-view. Orientation information can also be represented explicitly by displaying superior-inferior directions, etc.

Knowledge of such anatomical references may be used in minimally-invasive procedures in order to maintain spatial awareness, which can be easily lost when the surgeon are working with limited visibility.

Output Data

Following segmentation and identification, the output data generated may be any data that can be derived from the visual data.

The output data generated may be a record the location and orientation of the anatomical structure for future use (for example, to identify possible sources of bleeds. The output data may also or instead be an estimate of blood flow rate, flow direction, blood pressure or blood oxygenation.

The output data may also include measurement of the size or (relative) position over time of the anatomical structure, changes of characteristic features (colour, texture, etc.) of the anatomical structure, and quantification of such characteristics.

The results of this quantification activity can be utilized in several ways, depending upon the application. While results may be delivered directly within the monitoring system, it may also be possible to distribute results through connected systems such as a Surgical Navigation System.

The raw values of the output data may be provided to the surgeon 101 directly for use in decision making during the medical procedure. Such raw values may include distances between an object and a tracked tool, and pulse-rate of a blood vessel.

When data output values fall outside of an expected range, such an event may be flagged to the surgeon 101 using a combination of visual, auditory or tactile notification mechanisms as described above.

This output data may be further processed (either using traditional algorithmic approaches, or machine learning techniques) to elucidate features or changes in features which are indicative of situations that the surgeon 101 may not be able to notice in the normal course of the medical procedure.

Such features may include changes in heartrate or blood-flow between different vessels in the visual field, histopathology, development of a cerebral spinal fluid leak, identification of hypoxic tissue, and changes in a value which fall outside of the expected normal range (this may be established through configurable threshold, medical convention, preoperative imaging, or through observation of the patient prior to an intervention. As well, tension in tendons and ligaments may be quantified and tissue viability may also be quantified.

Virtual Representation

The virtual representation of the anatomical structure may also be presented in a number of ways.

For example, the segmented anatomical structure may be virtually emphasized through techniques such as outlining, desaturation, increased vibrancy, etc. Once a structure has been identified and segmented by the system, it is possible to apply any combination of many techniques in order to augment visualization or awareness of that structure. Such virtual representation may include: outlining, false-colour overlay, augmented-reality overlay, local contrast enhancement, sub-feature enhancement or annotation, reduction of visual impact/artefact, reducing glare from an unimportant element of the image, selectively desaturating an object, such as a blood-vessel), and diminished reality.

Such virtual representation may be applied directly to the current video frame, including a heatmap representing blood-oxygenation in an area of interest and lines showing the boundary of healthy vs pathological tissue. See FIGS. 11-12 for examples of virtual representations of the output data overlaid on the current visual information.

Events and Response

While a bleed scenario has been discussed, the monitoring method 400 may also be used in method 500 for detecting and reacting to other events during a medical procedure. Events that may be detected include those of a clinical nature related to the patient undergoing surgery and those related to the surgical environment.

Regarding patient events, as the surgeon 101 interacts with tissue, the tissue naturally undergoes physiological changes. Certain changes are indicative of a negative physiological condition requiring specific surgical intervention, or complications.

An example patient event is the detection of hypoxic tissue. When tissue is compressed or has blood flow restricted through other means, the tissue can enter a hypoxic state. It is during this state that the tissue integrity can be compromised. The monitoring system can utilize video processing (such as spectroscopic analysis) to detect when tissue hits a threshold for hypoxia and either alert the surgeon that reperfusion is necessary (such as removing a vessel clamp, or removing the tissue retraction) or automatically enacting that change without surgeon intervention.

Another patient event is the detection of positive response to a drug or biologic. When a drug, therapy, or biologic is applied during a surgical procedure, it can be difficult to determine the efficacy of that component. Real-time video processing and analysis can indicate the positive response, indicating an event that allows the surgeon to progress through the procedure.

A further patient event is the detection of proper achievement of surgical plan. A surgical plan can be simple or complex, but a surgeon can exit a procedure or phase of a procedure when certain criteria are met. Those criteria can be automatically detected and tracked as events, the combination of certain events can indicate achievement of a surgical goal. For example, real-time tracking of a tendon through motion can show the bony anatomy or tendon are in a state of ideal alignment, indicating the surgeon has properly affected the desired condition and it is time to proceed to the next part of the procedure.

Regarding environmental events, as the surgeon moves through the surgical workflow, different instruments, equipment, and environmental settings may be employed. Automatic detection of these changes through real-time or semi-real-time processing of video data may indicate an event which necessitates further reaction or changes.

One such environmental event is the detection of the introduction of a surgical instrument. When the surgeon introduces an instrument into the surgical field. Video processing and analysis techniques may be used to recognize the instrument, and may allow the system to enact a corresponding change of parameters on a multitude of systems in the operating room. For example, presence of a new tracked instrument on a video feed may indicate the need to change a setting on equipment designed to track instruments. As another example, the introduction of a surgical instrument while another surgical instrument is in the field may indicate a slightly different use of that second instrument.

Another environmental event is the detection of the introduction of surgical materials. When a surgeon is moving between different phases of the surgical procedure, and in particular when the surgeon is preparing to end a surgical procedure, certain hemostasis techniques and agents, adhesive compounds, and other biologics or supplies may be introduced. The introduction of these materials can alert surgical staff to the movement between phases of the procedure. For example, introduction of a biologic or component indicating completion of the procedure is an event indicating the imminent end of the procedure. Such actions may include coordination of closure activities in the OR and outside of the OR (recovery).

A further example of an environmental event is the detection of changes in environmental control. Certain changes in environmental control, for example, the turning on or off of the lights, indicate an event requiring a response on other equipment. Automatic detection of that event may drive subsequent automatic action on changes parameters (in the room light example, the light intensity from a surgical microscope which may now need to be adjusted).

Such changes may be detected/analyzed, segmented, and quantified. In response to the detected event, the generated information may be used to bring the surgeon's attention to the area, suggest a surgical intervention to the surgeon or the surrounding staff; for example, drawing the surgeon's attention to a bleeding vessel. Communication may be made outside of the operating room for further action or for calling ahead to recovery room to prepare for the patient Other action that may be taken include automatically suggesting or performing changes to surrounding surgical equipment required to enact the change. This may include adjusting equipment parameters, states, and/or settings. For example, the bipolar settings or the focus of the optical system may be changed, the lights may be turned off. Recording of data for post-operative analysis may be triggered, as well as marking video files for post-operative review of surgical technique. These video files may also be stored as evidence for insurance or to provide labeling.

Other events can be positive and indicate a positive response to a therapy or proper achievement of a surgical plan.

Although the above discussion refers to the surgeon as being the user who controls and uses the examples of the present disclosure, it should be understood that the present disclosure is not limited to any specific user. In some examples, there may be a plurality of users involved.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A monitoring system for providing visual enhancements during a medical procedure, the system comprising:
   a sensor for capturing visual information of a site during the medical procedure in real time, the sensor being a camera and the visual information being a video of a field-of-view (FOV) of the site during the medical procedure, the visual information comprising current visual information as a current frame of the video taken at a first point in time during the medical procedure;
   a memory for storing at least a portion of the visual information as stored visual information, the stored visual information having been captured at a second point in time during the medical procedure prior to the first point in time, the stored visual information being one or more past frames of the video;
   a display for displaying the current visual information; and
   a processor coupled to receive the current and stored visual information from the sensor and the memory, and coupled to transmit output data for display on the display, the processor being configured to:
      identify and compare a feature of interest in the current visual information at the first point in time and the stored visual information at the second point in time;
      generate feedback data associated with the feature of interest using the current visual information and the stored visual information; and
      cause the display to display a virtual representation of the feedback data overlaid on the current visual information.

2. The system of claim 1, wherein the processor is further configured to analyze the current or past frames according to at least one of colour, texture, physical shape, and location within the FOV for identifying the feature of interest.

3. The system of claim 2, wherein the processor is configured to segment an area in the at least one of the current and past frames according to the video analysis, and identify the segmented area as indicative of the feature of interest.

4. The system of claim 2, wherein the processor is configured to analyze the current frame to detect a colour indicative of a pool of blood, and the stored visual information is analyzed to identify the feature of interest related to the pool of blood.

5. The system of claim 4, wherein the feature of interest is a bleed point, and the feedback data indicates a location of the bleed point.

6. The system of claim 3, wherein the processor is configured to analyze the current or past frames to identify the segmented area as representing an anatomical structure.

7. The system of claim 6, wherein the anatomical structure is at least one of a blood vessel, a nerve, a ligament, a bone structure and a tumour.

8. The system of claim 7, wherein the virtual representation displayed includes a virtual representation of the segmented anatomical structure.

9. A system for reacting to an event during a medical procedure, the system comprising:
   an implementation system configured to perform the medical procedure and to perform predetermined steps in response to the event; and
   the monitoring system of claim 1 coupled to the implementation system, wherein the feedback data includes indication that the event has occurred; and
   the monitoring system configured to:
   analyze the current visual information to detect occurrence of the event;
   signal the implementation system to pause the medical procedure and initiate the predetermined steps in response to the event; and
   when the event is no longer detected, signal the implementation system to resume the medical procedure.

10. A monitoring method for use during a medical procedure, the method comprising:
    capturing visual information of a site during the medical procedure in real-time, the visual information being a video of a field-of-view (FOV) of the site during the medical procedure, the visual information comprising current visual information as a current frame of the video taken at a first point in time during the medical procedure;
    storing at least a portion of the visual information as stored visual information, the stored visual information having been captured at a second point in time during the medical procedure prior to the first point in time, the stored visual information being one or more past frames of the video;
    identifying and comparing a feature of interest in the current visual information at the first point in time and the stored visual information at the second point in time;
    generating feedback data associated with the feature of interest using the current visual information and the stored visual information; and
    displaying a virtual representation of the feedback data overlaid on the current visual information.

11. The method of claim 10, further comprising analyzing the current or past frames according to at least one of colour, texture, physical shape, and location within the FOV for identifying the feature of interest.

12. The method of claim 11, further comprising segmenting an area in the at least one of the current and past frames according to the video analysis; and wherein the identifying comprises identifying the segmented area as indicative of the feature of interest.

13. The method of claim 11, wherein the analyzing comprises detecting, in the current frame, a colour indicative of a pool of blood, and the stored visual information is analyzed to identify the feature of interest related to the pool of blood.

14. The method of claim 13, wherein the feature of interest is a bleed point, and the feedback data generated indicates a location of the bleed point.

15. The method of claim 12, wherein the segmented area is identified as representing an anatomical structure, the anatomical structure being the feature of interest.

16. The method of claim 15, wherein the displaying includes displaying a virtual representation of the anatomical structure.

17. A method for reacting to an event during a medical procedure, the method comprising:
    performing the method of claim 10, wherein the feedback data includes an indication that the event has occurred;
    the feedback data causing a pause to the medical procedure when the event is detected;
    initiating a response procedure; and
    resuming the medical procedure when the event is no longer detected.

18. The method of claim 17, wherein the event is a bleed and the response procedure is a bleed response procedure, the bleed response procedure comprises:
    changing the FOV and/or magnification of the video to focus on an identified bleed point, as the feature of interest, during the bleed response procedure.

* * * * *